Aug. 8, 1950 P. M. REEDY Plant Pat. 971
PEACH TREE
Filed Dec. 31, 1948
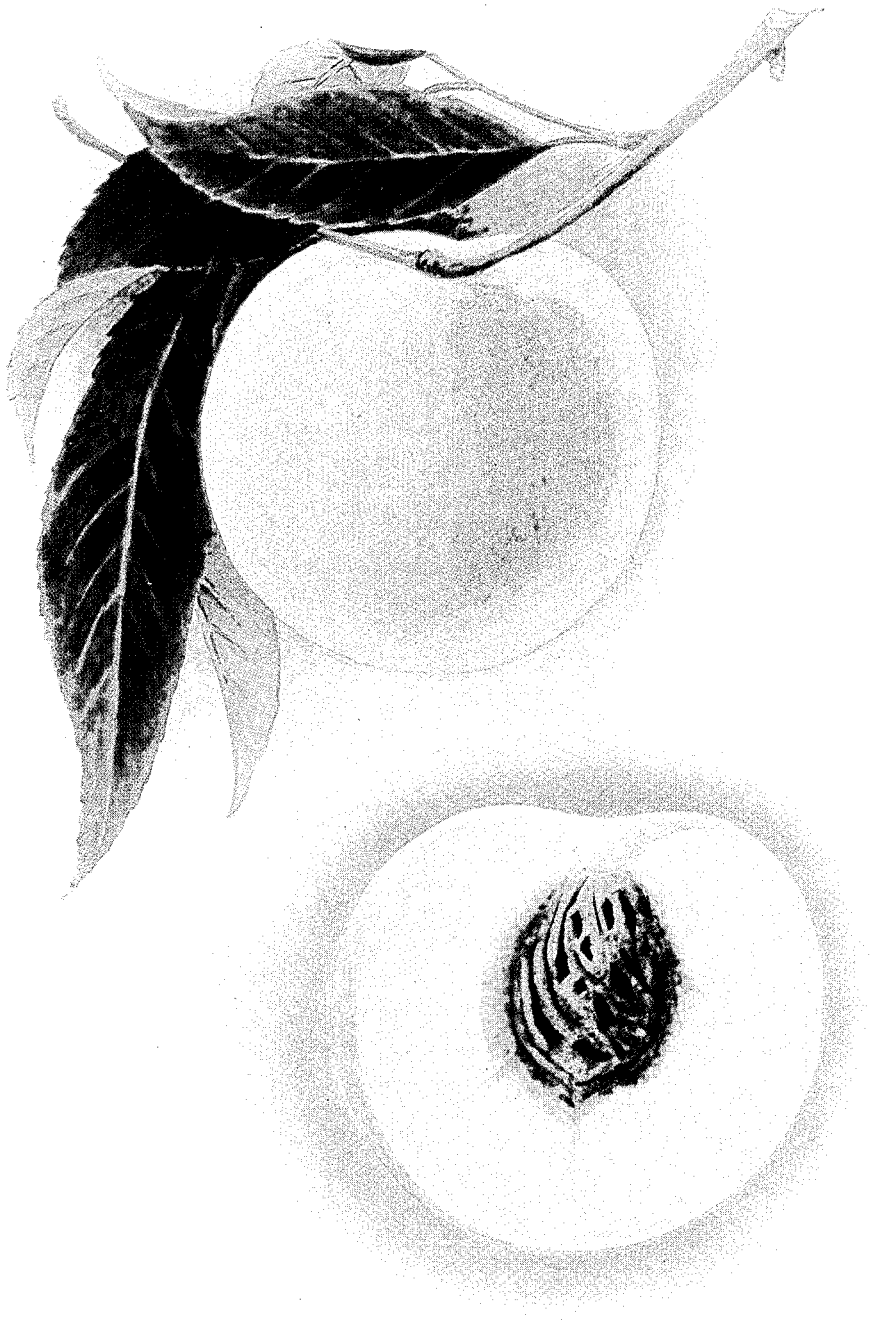
WITNESS
Addison F. Avery
INVENTOR
Perry M. Reedy
by Wright & Wright
ATTYS Patented Aug. 8, 1950

Plant Pat. 971

UNITED STATES PATENT OFFICE

971

PEACH TREE

Perry M. Reedy, Yuba City, Calif.

Application December 31, 1948, Serial No. 68,517

1 Claim. (Cl. 47—62)

The present discovery relates to a new and distinct variety of peach tree having freestone fruit; such fruit closely resembling the J. H. Hale in fruit type, but being distinguishable therefrom in several important characteristics.

Firstly, the fruit of the present variety ripens between the J. H. Hale and the Rio Oso Gem; the ripening period being in the latter part of August in California.

Secondly, the fruit when ripe is low, normally, in tannin content and therefore is subject to a minimum of oxidization and resultant discolorization when the flesh is cut and exposed to the air. Thus, in addition to being an excellent dessert peach, it is especially useful for processing by freezing, as there is no substantial or objectionable discolorization.

The herein claimed variety of peach tree was discovered in 1945 by the applicant on his ranch near Yuba City, California, and the original tree is believed to be a chance seedling. Since the discovery of the original tree, and the recognition of it as a new and distinct variety, the same has been successfully asexually reproduced. The reproduced trees, which came into bearing in August 1948, carry forward all the novel characteristics of the original parent tree. Careful observation of such reproductions, and comparison of them with the parent tree, gives full support to the facts recited above in this paragraph.

In the original drawings:

Fig. 1 is a perspective view of one of the peaches of the new variety, as attached to a twig with leaves.

Fig. 2 is a sectional view, taken axially of such peach, with the stone exposed.

Referring now in detail to the new and distinct variety of peach tree and its fruit, the following is a specific description, in outline, of the same; detailed identification of colors being by reference to Maerz and Paul, Dictionary of Color:

Tree: Large, vigorous, upright to spreading; vase formed. Very productive–productive. Regular bearer.

Trunk: Medium size; smooth.

Branches: Medium size; smooth; brown (Plate 7–E–12). *Lenticels.*—Medium–full; medium–small size.

Leaves: Average length, 6¾'' to 7½''; average width, 1⅞'' to 2⅛''. Large–medium size. Ovate, acuminate—lanceolate. Acutely pointed; medium thickness. Dark green (Plate 23–L–6). Smooth.

*Margin.*—Glandular—crenate.

*Petiole.*—Short, thick.

*Glands.*—Average number, two. Opposite. Large–medium. Reniform. Green. Position—petiole—some on base of blade. Stipules—dehiscent.

Flower Buds: Medium size; medium length. Plump. Oppressed. Pubescent.

Flowers: Average dates first and full bloom—March 10–20. Blooming date compared with other varieties—medium. Small size—average one inch or less in diameter. Petals—⅜'' long by ¼'' wide. Generally salmon colored—light pink near base, shading to red margins and tips.

*Stamens.*—Filiform, anthers small, orange yellow. Filiments deep pink, fading to lighter shades with maturity.

*Sepals.*—Deep reddish on the outside, except on margins of the tips; which are lighter, covered with a heavy short pubescence. Tips green on inside; less pubescence.

Fruit:

*Size.*—Uniform; large. Average diameter axially, 2⅞''–3⅛''; average transverse in suture plane, 3⅜''.

*Form.*—Uniform; symmetrical; globose.

*Suture.*—An inconspicuous line; shallow, with slight depression beyond pistil point.

*Ventral surface.*—Rounded; lips equal.

*Cavity.*—Flaring; rounded, with suture showing on one side. Average depth, ⅝''; average breadth, 1½''–1¾''.

*Base.*—Rounded.

*Apex.*—Rounded to elongated; slightly depressed. Pistil point—apical.

Skin: Thin; medium; free.

*Tendency to crack.*—None.

*Down.*—Moderate; medium short.

*Color.*—Yellow to Deep Yellow ground (Plate 9–J–6 to Plate 9–J–2), Blushed Red, washed Bright Red, striped Dark Red on highly colored fruit. (Blush generally Plate 3–J–10 to plate 6–L–10.)

Flesh: Yellow to Deep Yellow (Plate 9–L–6, shading into plate 9–K–8); streaked, mottled with Red next to stone (Plate 6–K–6). Surface of pit cavity red with white-yellow fibers.

*Amygadalin.*—Scant; wanting.

*Juice.*—Moderate.

*Texture.*—Firm, medium. Fine; melting.

*Fibres.*—Few; fine; tender.

*Ripens.*—Evenly.

*Flavor.*—Subacid.

*Aroma.*—Distinct.

*Eating quality.*—Good–best.

Stone: Free. Parts from flesh smoothly.

*Size.*—Large. Average length, 1½–1 9/16″; average breadth, 1¼″ to 1 5/16″; average thickness, 1–1¼″.

*Form.*—Oval to obovoid; full.

*Base.*—Straight.

*Hilum.*—Oval.

*Apex.*—Rounded; pointed.

*Sides.*—Equal.

*Surface.*—Irregularly furrowed near base.

*Ventral edge.*—Pitted and grooved from base throughout. Thin; without wing.

*Ridges.*—Jagged; interrupted.

*Pits.*—Circular.

*Dorsal edge.*—Narrow, with shallow, narrow groove throughout.

*Color of stone.*—Dark brown.

*Tendency to split.*—Slight.

Use: Dessert; canning; freezing.

Keeping quality: Good.

Resistance to insects: Medium.

Resistance to disease: Medium.

Shipping quality: Good; medium.

The primary distinguishing characteristics of the herein claimed new and distinct variety of peach tree, as compared to the J. H. Hale, which it most resembles, are the ripening period, which is between the J. H. Hale and the Rio Oso Gem, being in the latter part of August in California; and the normally low tannin content of the fruit when ripe. This normally low tannin content minimizes oxidization and discolorization of the flesh when it is cut and exposed to the air, and consequently the peach is admirably adapted to the frozen food industry, and can be processed, frozen, and ultimately thawed for use without objectionable discolorization.

Having thus described my discovery, I claim:

A new and distinct variety of peach tree, substantially as shown and described, characterized by comparison with the J. H. Hale freestone peach which it most closely resembles, by a ripening period between said J. H. Hale and the Rio Oso Gem, and by a normally low tannin content by reason of which the flesh when cut and exposed to the air is subject to a minimum of oxidization and discolorization; the fruit being large, uniform, and globose; the skin being a deep yellow ground color blushed red, and the flesh being a yellow to deep yellow color streaked and mottled with red next to the stone.

PERRY M. REEDY.

No references cited.